United States Patent [19]

Twisselmann et al.

[11] Patent Number: 4,723,842
[45] Date of Patent: Feb. 9, 1988

[54] STEREOSCOPIC SURGERY MICROSCOPE FOR EYE SURGERY WITH SELECTIVE IMAGE REVERSAL

[75] Inventors: Lorenz Twisselmann, Prisdorf; Josef Reiner, Rodenkirchen, both of Fed. Rep. of Germany

[73] Assignee: J. D. Moller Optische Werke GmbH, Fed. Rep. of Germany

[21] Appl. No.: 872,500

[22] Filed: Jun. 10, 1986

[30] Foreign Application Priority Data

May 10, 1986 [DE] Fed. Rep. of Germany ....... 3615842

[51] Int. Cl.$^4$ .......................... G02B 7/18; G02B 23/02
[52] U.S. Cl. .................................. 350/511; 350/518; 350/569; 350/287; 350/519
[58] Field of Search ............... 350/511, 520, 519, 569, 350/287, 286, 513, 514, 515, 559, 572, 622, 623, 518

[56] References Cited

U.S. PATENT DOCUMENTS

| 2,901,943 | 9/1959 | Tackaberry | 350/286 |
| 3,645,602 | 2/1972 | Clave et al. | 350/559 |
| 4,047,794 | 9/1977 | Park et al. | 350/511 |
| 4,367,949 | 1/1983 | Lavering | 350/286 |
| 4,571,038 | 2/1986 | Juko | 350/515 |

FOREIGN PATENT DOCUMENTS

| 444823 | 5/1927 | Fed. Rep. of Germany | 350/286 |
| 558538 | 1/1975 | France | 350/511 |
| 420565 | 12/1934 | United Kingdom | 350/286 |

Primary Examiner—Jon W. Henry
Attorney, Agent, or Firm—Allegretti, Newitt, Witcoff & McAndrews, Ltd.

[57] ABSTRACT

The subassembly arranged between a zoom system and the ocular telescope of a stereoscopic surgery microscope for eye surgery comprises a prism system, arranged in a casing, for a complete image reversal with a beam displacement and a direction-invariable optical path, it being possible to move the prism system out of the optical path between the zoom system and the ocular telescope for eliminating image reversal.

6 Claims, 4 Drawing Figures

STEREOSCOPIC SURGERY MICROSCOPE FOR EYE SURGERY WITH SELECTIVE IMAGE REVERSAL

BACKGROUND OF THE INVENTION

The present invention relates to a subassembly for a stereoscopic surgery microscope for eye surgery for positioning between a zoom system and an ocular telescope.

Ophthalmoscopy deals with the observation of the eyeground by means of an ophthalmoscope. For indirect ophthalmoscopy a convex mirror and an intermediately positioned convex lens are used for producing a reversed, minified, low luminosity image with a large field of view. By using an indentation lens, comprising a contact lens with three additional mirrors positioned at different angles, so that a laterally displaced image is obtained, an improved and more plastic fundus image is obtained. In addition, stereomicroscopes are known, which have separate objectives or have one objective for the purpose of the magnified observation of the eye during eye surgery. The use of an ophthalmoscope lens for observing the retina and parts of the vitreous body of the eye is also known for extending the possible uses of surgery microscopes in ophthalmology. However, a use problem is the reversed image observed through the microscope and which makes it difficult, or even almost impossible to handle instruments in the visual field.

SUMMARY OF THE INVENTION

The problem of the present invention is to provide a subassembly for a stereoscopic surgery microscope for eye surgery of the aforementioned type permitting a complete image reversal without direction change of the optical path, but with a beam displacement, so that a compact construction is obtained. Thus, when the subassembly is used with an ophthalmoscope lens placed in front of the surgery microscope, together with a contact lens which can be placed directly on the eye and which produces an inverted image of the retina, it can be used for producing an upright steroscopic image of the retina.

According to the invention this problem is solved by a subassembly of the aforementioned type which, according to the invention, comprises a prism system arranged in a casing for a complete image reversal with a beam displacement and a direction-invariable optical path, the prism system comprising a pentagonal prism with a roof edge and a semiparallelepipedic prism or a pentagonal prism with a semiparallelepipedic prism with roof edge.

Advantageous developments of the invention are characterized in the subclaims.

Such a subassembly constructed for surgery microscopes permits an image reversal with a lateral beam displacement and an optical path without direction change, so that the image reversal obtained can be used for image erection when using a contact lens, which when placed directly on the eye produces an inverted image of the retina. Furthermore the subassembly with its image reversal can be used as an ophthalmoscope lens, which can be fitted as an attachment in front of a surgery microscope. In addition, the subassembly makes it possible to manufacture equipment with a compact construction.

BRIEF DESCRIPTION OF THE DRAWINGS

The invention is described in greater detail hereinafter relative to the attached diagrammatic side views, wherein show.

DETAILED DESCRIPTION OF THE PREFERRED EMBODIMENTS

Figure 1:
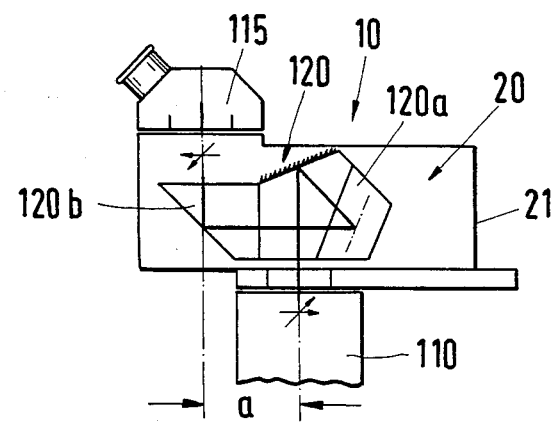
FIG. 1 A surgery microscope with a subassembly arranged between the zoom system and the ocular telescope.
Figure 2:
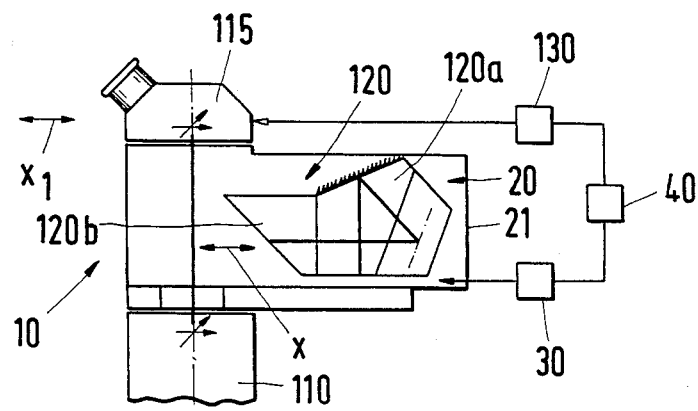
FIG. 2 The surgery microscope according to FIG. 1, but with the prism system extended out of the optical path for removing the image reversal.

The surgery microscope 10 shown in FIGS. 1 and 2 has a zoom system 110 constructed in per se known manner and an ocular telescope 115.

Between zoom system 110 and ocular telescope 115 is arranged a subassembly 20, which comprises a prism system 120 arranged in a casing 21 and which is constructed in such a way that a complete image reversal is obtained with beam displacement and an optical path without direction change.

This prism system 120 comprises a pentagonal prism 120a with roof edge and a semiparallelepipedic prism 120b (half cube prism) or a pentagonal prism with a semiparallelepipedic prism with roof edge.

In order to be able to eliminate the image reversal, the prism system 120 is displaceably arranged in the direction of arrow X in the interior of casing 21 of subassembly 20. Prism system 120 is e.g. displaced by means of a drive motor 30 via a worm drive or some other suitable advance means. If the prism system 120 is moved out of the optical path of the microscope, as shown in FIG. 2, then the image reversal is eliminated. However, the ocular telescope 115 is also arranged displaceably in the direction of arrow X1 by the amount of the optical displacement a on the casing 21 of subassembly 20, the displacement being brought about by per se known means. The necessary drive mechanism is indicated at 130 in FIG. 2. The displacement of the ocular telescope 115 and/or the prism system 120 is e.g. controllable by means of a control mechanism 40, but a manual displacement is also possible.

Figure 3:
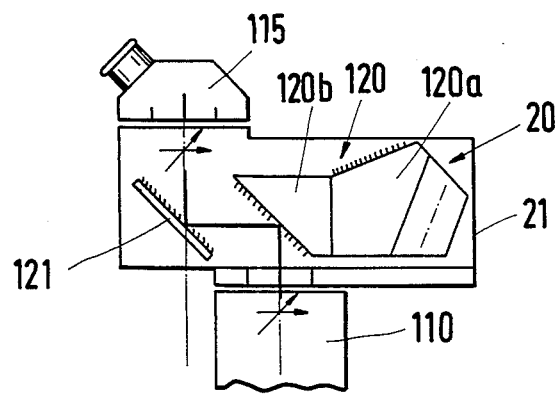
FIG. 3 Another embodiment of a surgery microscope with a mirror associated with the prism system.
Figure 4:
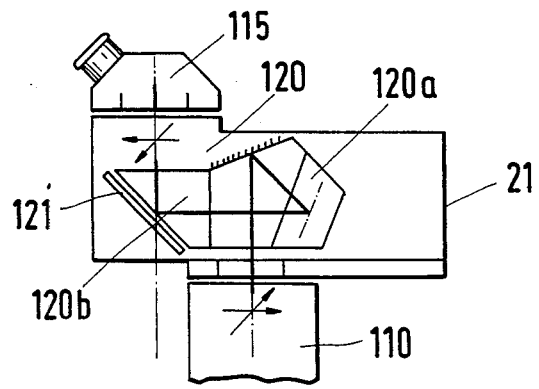
FIG. 4 The surgery microscope according to FIG. 3, but with the prism system introduced into the optical path.

In the case of the embodiment shown in FIGS. 3 and 4, apart from prism system 120, casing 21 contains a mirror 121, which is positioned in such a way that its reflecting surface is located very close, i.e. with a limited spacing with respect to the externally reflected 45° surface of the semiparallelepipedic prism 120b (FIG. 4). In the case of a displacement of prism system 120 in casing 21 (FIG. 3), the optical path is reflected on the outer face of the semiparallelepipedic prism 120b and on mirror 121 and consequently the image reversal is eliminated, but the beam displacement is retained, so that there is no need to move the ocular telescope 115. In this embodiment the prism system 120 is moved in the same way as with the embodiment according to FIGS. 1 and 2.

What is claimed is:

1. A microscope for stereoscopic eye surgery comprising an ocular telescope,
a zoom lens system, a prism system interposed between said ocular telescope and said zoom lens system to provide complete image reversal and beam displacement with directional change of the beam upon passage through said prism system characterized by means for moving said prism system out of the optical path between said zoom lens system and said ocular telescope to eliminate image reversal.

2. The microscope of claim 1 wherein said prism system includes a casing enclosing said prism system and on which said ocular telescope is mounted, means for moving said ocular telescope and said prism system simultaneously, thereby displacing said ocular telescope by the amount of the beam displacement.

3. The microscope of claim 2 which includes motor drive means for moving said ocular telescope.

4. The microscope of claim 2 wherein said prism system comprises a pentagonal prism with roof edge and a half cube prism or a pentagonal prism and a half cube prism with a roof edge.

5. The microscope of claim 4 wherein said half cube prism has an outwardly reflecting 45° surface and a mirror, the reflecting surface of which is spaced a very small distance from said outwardly reflecting 45° surface.

6. The microscope of claim 5 wherein said mirror is fixed so that when said prism system is moved out of the optical path, the optical beam is reflected on the outer face of said half cube prism and on the mirror, the image reversal is eliminated and the beam displacement is retained.

* * * * *